(12) United States Patent
Morales

(10) Patent No.: US 9,332,989 B2
(45) Date of Patent: May 10, 2016

(54) SURGICAL INSTRUMENT FOR REMOVING SURGICAL CLIPS

(71) Applicant: Aesculap AG, Tuttlingen (DE)

(72) Inventor: Pedro Morales, Tuttlingen-Nendingen (DE)

(73) Assignee: Aesculap AG, Tuttlingen (DE)

( * ) Notice: Subject to any disclaimer, the term of this patent is extended or adjusted under 35 U.S.C. 154(b) by 605 days.

(21) Appl. No.: 13/741,507

(22) Filed: Jan. 15, 2013

(65) Prior Publication Data

US 2013/0150870 A1   Jun. 13, 2013

Related U.S. Application Data

(63) Continuation of application No. PCT/EP2011/061898, filed on Jul. 12, 2011.

(30) Foreign Application Priority Data

Jul. 28, 2010   (DE) .......................... 10 2010 036 713

(51) Int. Cl.
| | | |
|---|---|---|
| *A61B 17/10* | (2006.01) | |
| *A61B 17/076* | (2006.01) | |
| *A61B 17/00* | (2006.01) | |
| *A61B 17/122* | (2006.01) | |
| *A61B 17/28* | (2006.01) | |
| *A61B 17/29* | (2006.01) | |

(52) U.S. Cl.
CPC ............. *A61B 17/105* (2013.01); *A61B 17/076* (2013.01); *A61B 17/00234* (2013.01); *A61B 17/122* (2013.01); *A61B 2017/2837* (2013.01); *A61B 2017/2929* (2013.01); *A61B 2017/2933* (2013.01)

(58) Field of Classification Search
CPC ............. A61B 17/128; A61B 17/1285; A61B 17/076; A61B 17/0487; A61B 17/10; A61B 2017/049; A61B 2017/0488; A61B 17/105; B25B 27/00; B25B 27/146; Y10T 29/53657; Y10T 29/53683; B25C 11/00–11/02
USPC ......... 606/138, 139, 142, 151, 157, 205–207; 81/485, 486; 433/4
See application file for complete search history.

(56) References Cited

U.S. PATENT DOCUMENTS

| | | | |
|---|---|---|---|
| 439,994 A | | 11/1890 | Ballard |
| 600,504 A | * | 3/1898 | Autio .............................. 81/488 |
| 4,171,701 A | * | 10/1979 | Walter et al. ................... 606/133 |
| 4,635,634 A | * | 1/1987 | Santos ........................... 606/142 |
| 4,887,612 A | * | 12/1989 | Esser et al. .................... 600/564 |

(Continued)

FOREIGN PATENT DOCUMENTS

| | | |
|---|---|---|
| DE | 94 06 926 | 9/1994 |
| JP | 2009501570 | 1/2009 |

(Continued)

*Primary Examiner* — Todd E Manahan
*Assistant Examiner* — Charles Wei
(74) *Attorney, Agent, or Firm* — Lipsitz & McAllister, LLC

(57) ABSTRACT

The invention relates to a surgical instrument for removing a surgical clip applied to a hollow organ, said clip comprising two clamping arms having two free ends and two ends connected to each other and defining a connecting region, and said instrument having a proximal and a distal end, wherein a spreading device for grasping and spreading apart an applied clip from an applied position to a released position is arranged at the distal end.

22 Claims, 11 Drawing Sheets

(56) References Cited

U.S. PATENT DOCUMENTS

| | | | |
|---|---|---|---|
| 5,312,420 A | 5/1994 | Toso et al. | |
| 5,707,377 A * | 1/1998 | Keller et al. | 606/138 |
| 5,752,973 A * | 5/1998 | Kieturakis | 606/207 |
| 6,824,548 B2 * | 11/2004 | Smith et al. | 606/143 |
| 2004/0044352 A1 * | 3/2004 | Fowler et al. | 606/142 |
| 2004/0044363 A1 * | 3/2004 | Fowler | 606/205 |
| 2005/0119677 A1 | 6/2005 | Shipp | |
| 2006/0201130 A1 * | 9/2006 | Danitz | 59/78.1 |
| 2007/0093856 A1 * | 4/2007 | Whitfield et al. | 606/142 |
| 2008/0255608 A1 * | 10/2008 | Hinman et al. | 606/205 |
| 2009/0012545 A1 * | 1/2009 | Williamson et al. | 606/157 |
| 2012/0059400 A1 | 3/2012 | Williamson, IV et al. | |
| 2013/0150870 A1 * | 6/2013 | Morales | 606/143 |

FOREIGN PATENT DOCUMENTS

| | | |
|---|---|---|
| WO | WO 96/16602 | 6/1996 |
| WO | WO 2007/009099 | 1/2007 |

* cited by examiner

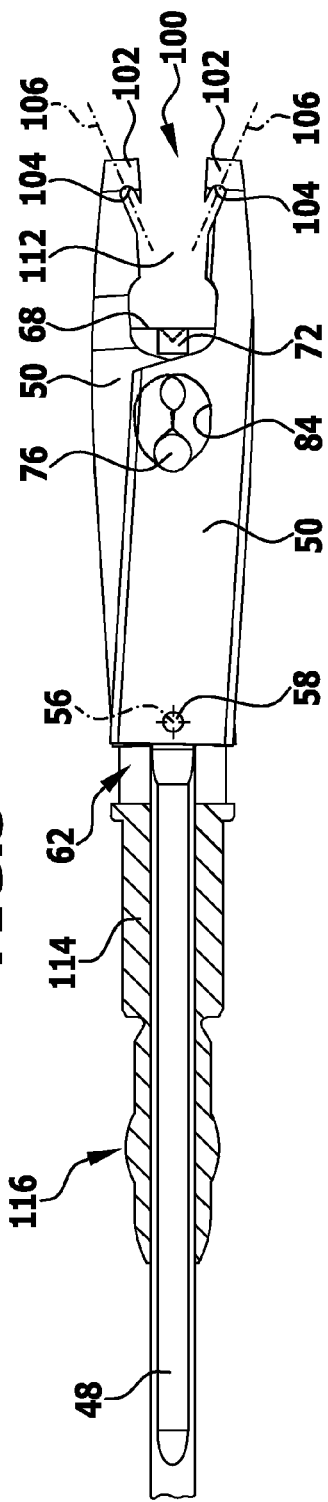
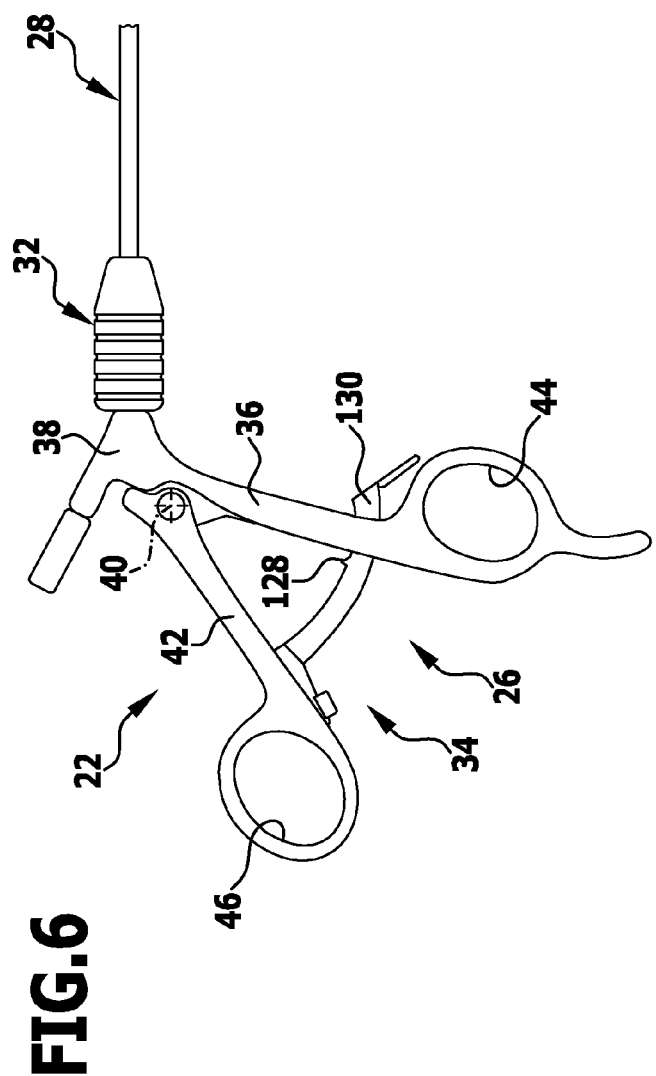
FIG.5
FIG.6 under Jul. 28, 2010, which are incorporated herein by

SURGICAL INSTRUMENT FOR REMOVING SURGICAL CLIPS

CROSS-REFERENCE TO RELATED APPLICATIONS

This application is a continuation of international application number PCT/EP2011/061898 filed on Jul. 12, 2011 and claims the benefit of German application number 10 2010 036 713.3 filed on Jul. 28, 2010, which are incorporated herein by reference in their entirety and for all purposes.

FIELD OF THE INVENTION

The present invention relates to a surgical instrument for removing a surgical clip applied to a hollow organ generally, and more specifically to a surgical instrument for removing a surgical clip applied to a hollow organ, the clip comprising two clamping arms having two free ends and two ends connected to each other and defining a connecting region, and the instrument having a proximal and a distal end.

BACKGROUND OF THE INVENTION

In surgery, surgical clips, in particular, in the form of so-called ligature clips, are increasingly being used for hemostasis of blood vessels and for clamping and occluding other hollow organs. The clips may comprise two clamping arms extending substantially parallel and having two free ends and two ends connected to each other and having a connecting region. So-called double-shank clips, for example, are also used. These comprise a total of four clamping arms with four free ends which are connected in pairs, and four ends also connected in pairs and defining two connecting regions. With such double-shank clips, which may be formed from a wire ring closed within itself, vessels or hollow organs can even be easily occluded at two locations separate from each other.

The placement of clips is considerably easier and quicker than suture techniques used heretofore. As they normally remain as implant in the body, the clips are manufactured from biocompatible materials, in particular, from pure titanium or a titanium alloy.

In an operation, before a blood vessel or a hollow organ can be severed, it is usually occluded with at least two, even better with three clips so that a surgeon can sever the hollow organ between two placed clips without blood or other body fluids issuing.

Every now and then one or more clips are wrongly positioned, for example, at a wrong vessel or hollow organ. If such a situation arises, the clips have to be removed again in order that the original functioning of the vessel or hollow organ can be reestablished. In so-called open surgery, removal of wrongly positioned clips, for example, using needle holders, forceps or other instruments is usually still possible, albeit with a very great effort. In endoscopic procedures, the wrong positioning of a clip is extremely critical. The clips are usually very small and are also constructed so as not to have undercuts or other protruding components, which would make them easy to grasp. Nor is this desirable for in the ideal case the two clamping arms of the clip, also referred to as clip legs, or two clamping arms of each pair in a double-shank clip, lie congruently one upon the other without any gap.

SUMMARY OF THE INVENTION

In a first aspect of the invention, a surgical instrument for removing a surgical clip applied to a hollow organ is provided. Said clip comprises two clamping arms having two free ends and two ends connected to each other and defining a connecting region. Said instrument has a proximal and a distal end. A spreading device for grasping and spreading apart an applied clip from an applied position to a released position is arranged at the distal end.

BRIEF DESCRIPTION OF THE DRAWING FIGURES

The foregoing summary and the following description may be better understood in conjunction with the drawing figures, of which:

FIG. 5 shows a view of the spreading device in analogy with FIG. 3 in the clip receiving position;

FIG. 6 shows a view of the instrument handle in analogy with FIG. 4 in the clip receiving position;

DETAILED DESCRIPTION OF THE INVENTION

Figure 1:
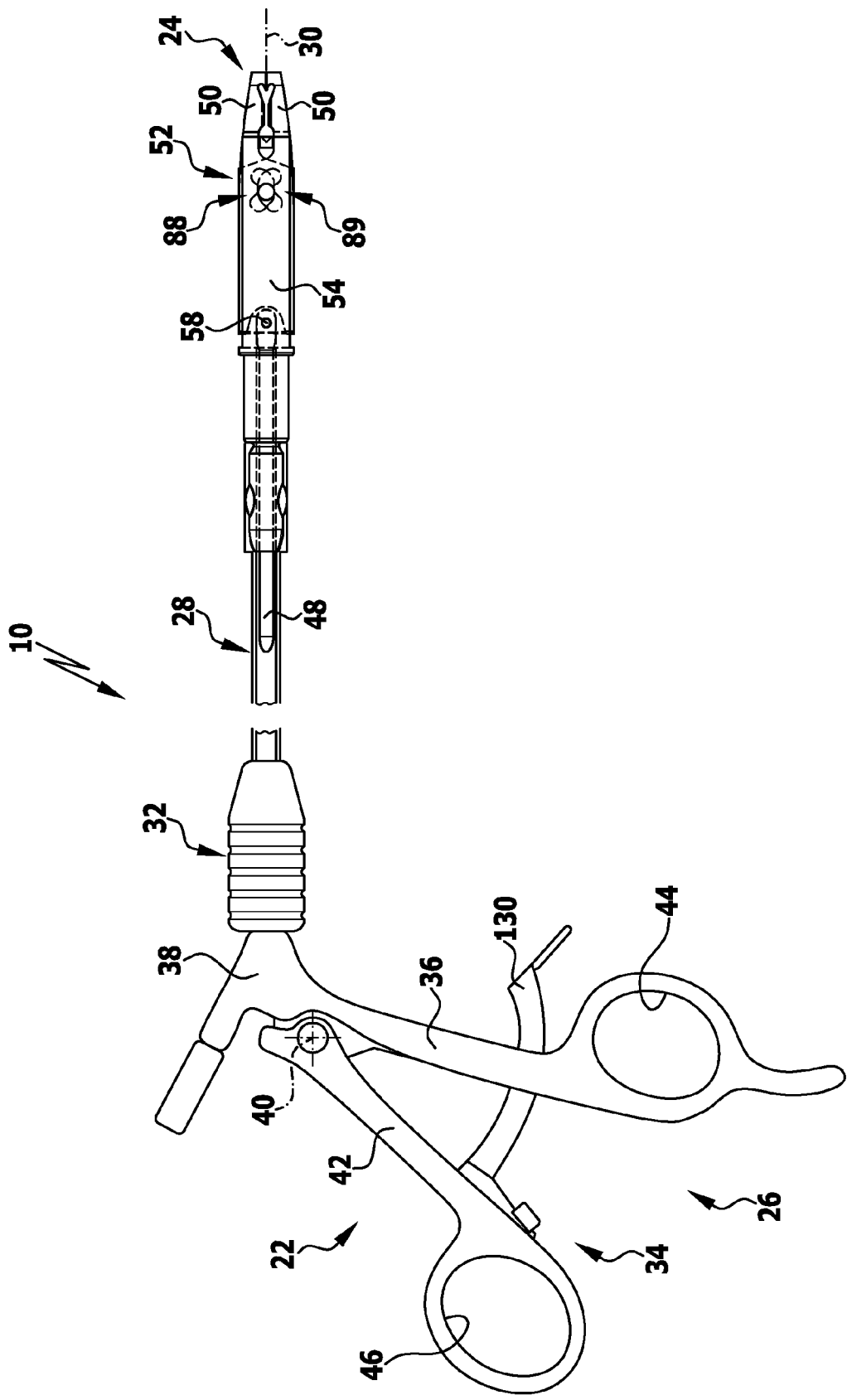
FIG. 1 shows a diagrammatic, partly broken-open side view of a surgical instrument for removing a surgical clip applied to a hollow organ.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical instrument for removing a surgical clip applied to a hollow organ, said clip comprising two clamping arms having two free ends and two ends connected to each other and defining a connecting region, and said instrument having a proximal and a distal end, wherein a spreading device for grasping and spreading apart an applied clip from an applied position to a released position is arranged at the distal end.

If, for example, the instrument is configured in the form of an endoscopic instrument, it is then also possible for a clip to be removed to be easily grasped and spread apart with the spreading device through a small access into a patient's body so as to carefully and safely remove it from a blood vessel or hollow organ, for example, where it was, in particular, wrongly placed. The spreading device is, in particular, constructed such that further instruments are not required for removal of the clip. The clip is preferably automatically removable with the spreading device. It is preferably held safely with the instrument after the spreading-apart and can be removed again through an, in particular, minimally invasive access into the human body, made, for example, by a trocar.

It is advantageous if the spreading device comprises a clip receptacle and if it is transferable from an insertion position in which it defines a minimal cross-sectional area to a clip receiving position in which the clip receptacle is open to receive the clip to be removed. The clip receptacle enables safe grasping of the clip. In the insertion position, the spreading device needs very little space, so that it can also be inserted through a small, in particular, minimally invasive access into a patient's body. In the clip receiving position, the clip can be introduced into the clip receptacle and received in it.

It is also advantageous if the spreading device comprises a clip receptacle, and if it is transferable from a clip receiving position in which the clip receptacle is open to receive the clip to be removed to a clip spreading position in which the clip to be removed can be held spread apart in the clip receptacle. A spreading device of such construction enables a clip to be received and spread apart so long as it is held in the clip receptacle. Owing to the spreading-apart, it can be released from a vessel or hollow organ again, in particular, by the clamping arms, which, in the case of a simple, applied clip, essentially lie one against the other, being spread apart due to deformation of the connecting region caused by these pivoting away from each other. In the case of a double-shank clip, in particular, the two connecting regions lying against each other in an applied or closed position can be spread apart.

In accordance with a further preferred embodiment of the invention, it may be provided that the spreading device comprises a clip receptacle and that it is transferable from a clip spreading position in which the clip to be removed is held spread apart in the clip receptacle to a clip removal position in which the clip to be removed can be held closed in the clip receptacle. The spreading device of such construction makes it possible, in particular, to hold the spread-apart clip and, for example, after the clip has been moved away from the vessel or hollow organ, to close it again and hold it in the closed position. This facilitates, in particular, extraction of the clip from the patient's body through a minimally invasive access. In principle, it is conceivable to also move the clip out of a patient's body in the spread-apart position. However, this would require significantly larger cross sections of the accesses.

The construction of the instrument is particularly simple if the clip removal position and the insertion position are identical. This allows the instrument to be transferred from the insertion position to the clip receiving position, the clip to be received, the clip to then be spread apart by transferring the instrument from the clip receiving position to the clip spreading position, and, finally, after transferring the instrument from the clip spreading position to the clip removal position, which corresponds to the insertion position, the clip to be extracted from the patient's body.

To prevent movement of the clip relative to the spreading device and to enable it to be securely grasped and held by it, it is advantageous if the spreading device comprises at least one proximal and at least one distal clip receiving stop, which delimit the clip receptacle at the proximal side and at the distal side. In particular, the clip receiving stops may be of such construction that movement transversely to a connecting direction between proximal and distal clip receiving stops is not possible either. This prevents the clip from being able to fall out of the clip receptacle when it lies at the proximal side and the distal side against the respective proximal and distal clip receiving stops.

It is advantageous for two clip receiving stops to be provided at the distal side. In particular, each of the two clip receiving stops at the distal side can be adapted in its shape to one of the two free ends of the clamping arms of a simple clip or to one of the two connecting regions of a double-shank clip.

The at least one proximal and the at least one distal clip receiving stop are preferably arranged so as to be movable relative to each other. For example, they may be constructed so as be movable towards each other or away from each other in order to move the free ends of the clamping arms of the clip received in the clip receptacle relative to the connecting region or the connecting regions, for example, in order to spread the clip apart and, possibly, close it again.

To facilitate the spreading-apart of a clip, it is advantageous if a spacing in the longitudinal direction between the at least one proximal and the at least one distal clip receiving stop is alterable. In this way, it is, in particular, also possible to alter a spacing between free ends of the clamping arms of the clip to be removed and its connecting region or its connecting regions, which, for example, can be used to spread the clip apart.

The spacing advantageously decreases during transfer from the clip receiving position to the clip spreading position. In this way, it is possible to apply a spreading force in the longitudinal direction to the clip to be removed in order to move free ends of the clamping arms of a simple clip or connecting regions lying against each other in an applied position away from each other so as to release a vessel or hollow organ.

It is advantageous if a transverse spacing between the two clip receiving stops at the distal side increases transversely to the longitudinal direction during transfer from the clip receiving position to the clip spreading position. Owing to movement of the clip receiving stops at the distal side away from each other, free ends of the clamping arms of a simple clip or connecting regions of a double-shank clip lying against each other in an applied position can, if they are lying against the respective distal clip receiving stops, be easily moved away from each other, so that the clip can release a vessel or hollow organ.

To form, in particular, an endoscopic instrument, it is advantageous if the instrument comprises an elongate shaft, at the distal end of which the spreading device is arranged.

The construction of the instrument is particularly simple if the at least one proximal clip receiving stop and the shaft are arranged so as to be immovable relative to each other. In this way, in particular, a clip can be received in a defined manner in the clip receptacle, in particular, by the proximal stop being advanced towards the connecting region of a simple clip or towards free ends of a double-shank clip and applied to this connecting region or these free ends.

It is advantageous if the at least one distal clip receiving stop and the shaft are arranged so as to be movable relative to each other. This allows a surgeon to position the shaft with the proximal clip receiving stop, for example, at the connecting region of the clip and to hold it there, with all other movements of the at least one distal clip receiving stop then occurring relative to the shaft. There is then no necessity for a surgeon to adjust the instrument shaft relative to the clip. It should nevertheless be noted that it is, for example, also possible to arrange the distal clip receiving stop so as to be immovable relative to the shaft and then to construct the at least one proximal clip receiving stop so as to be movable relative to the shaft.

A clip can be spread apart particularly easily if the at least one distal clip receiving stop is arranged so as to be pivotable about a pivot axis relative to the shaft. It is, for example, thus possible for a free end of a clamping arm to be pivoted relative to the connecting region or for two connecting regions to be pivoted relative to the free ends of the clamping arms.

The pivot axis advantageously extends transversely to a longitudinal axis defined by the shaft. This facilitates handling of the instrument as it is thus possible for a clip to be received and spread apart by the spreading device, in particular, parallel to a longitudinal axis defined by it.

The spreading device can be of particularly compact construction if the two distal clip receiving stops are mounted so as to be pivotable about a common pivot axis relative to each other. For example, it is also possible for one of the two distal clip receiving stops to be arranged stationarily relative to the shaft and for only one to be constructed so as to be movable, in particular, pivotable, relative to the shaft.

In accordance with a further preferred embodiment of the invention, it may be provided that the spreading device comprises two tool elements movable relative to each other, and that the at least one distal clip receiving stop is arranged or formed on the two tool elements. In particular, only one of the two tool elements may be fitted with a distal clip receiving stop. The tool elements may, in particular, define an orientation of the clip receiving stops and, in the insertion position, be oriented parallel or also transversely to a longitudinal direction of the shaft.

Each tool element preferably comprises a distal clip receiving stop. For example, each distal clip receiving stop may be applied to a free end of the clip arms or to a connecting region of the clip in order to then spread apart the clip to be removed as a result of movement of the tool elements relative to each other.

In order to have to expose as little tissue as possible around the clip to be removed, it is advantageous if the at least one distal clip receiving stop is arranged or formed in the region of distal ends of the tool elements.

To provide an opening that is as large as possible for receiving a clip to be removed in the clip receiving position, it is advantageous if the two tool elements are mounted so as to be movable relative to the shaft. In particular, it is then also possible to dispense with a movability of the at least one proximal clip receiving stop relative to the shaft.

The instrument can be of particularly simple construction if the two tool elements are mounted so as to be displaceable and/or pivotable relative to the shaft. For example, a pivot axis for the two tool elements may be oriented transversely, in particular, perpendicularly, to a longitudinal direction of the shaft.

In accordance with a further preferred embodiment, it may be provided that the two tool elements are movably coupled to a force-transmitting member, mounted so as to be movable in or on the shaft, for moving the tool elements relative to each other as a result of movement of the force transmitting member. In particular, it is thus easily possible for movement of the two tool elements relative to each other, for example, displacement and/or pivotal movement of these relative to each other and possibly also relative to the shaft, to be enforced by moving the force-transmitting member, for example, a push-and-pull member in the form of a push-and-pull rod.

In principle, it is possible to provide the spreading device only in connection with a shaft or a short shaft portion. The instrument does, however, also advantageously comprise an actuating device for actuating the spreading device. In particular, this may be coupled to the force-transmitting member.

The actuating device is advantageously configured to move the two tool elements relative to each other. This enables particularly easy handling of the instrument as a surgeon, by actuating the actuating device, can, for example, move tool elements mounted at a distal end of a shaft so as be movable relative to each other.

It is advantageous, in particular, if the actuating device and the force-transmitting member are movably coupled to each other for transmitting an actuating force from the actuating device to the force-transmitting member.

This configuration allows a surgeon, merely by handling the actuating device, to move the force-transmitting member and, if it is coupled to one or both of the tool elements, to also position these in the desired way relative to each other.

The handling of the instrument is particularly easy for a surgeon if the actuating device is arranged or formed at the proximal end of the instrument. For example, he is then able, from outside a patient's body, to grasp in a targeted manner a clip that is to be removed from inside the patient's body, spread it apart and, in particular, remove it from the patient's body through a minimally invasive access.

It is advantageous if the two tool elements in the insertion position and/or in the clip removal position assume a closed position. This configuration enables, in particular, easy insertion and withdrawal of the instrument from a patient's body through a minimally invasive access.

In the closed position, the two tool elements advantageously lie at least in some sections against each other. They thus mutually form stops for delimiting movement towards each other. The clip receptacle can therefore also be defined in a simple way so as to ensure that clips to be removed can also be grasped and held in the defined and desired way.

In accordance with a further preferred embodiment of the invention, a connecting link guide may be provided for defining a pivotal movement of the two tool elements relative to each other as a result of displacement of the force-transmitting member in the longitudinal direction. It is possible to ensure, in particular, a defined movement for opening and closing the tool elements, also referred to as jaw parts, by designing the connecting link guide correspondingly. The connecting link guide enables, in particular, transformation of a linear movement into a pivotal movement or a movement perpendicular to the longitudinal axis.

The instrument is particularly simple in its construction if the connecting link guide is configured in the form of a slot-cam guide with a guide slot and a cam held and guided in the guide slot, the guide slot being arranged or formed on the shaft or on a tool element, and the corresponding cam on the respective other part. In particular, relative movement between the tool elements and, possibly, also relative to the shaft can thus be achieved by relative movement of cam and guide slot(s).

It is advantageous if each tool element comprises a guide slot, and if a cam held on the shaft is guided in the two guide slots. For example, as a result of relative movement of the guide elements in the longitudinal direction of the shaft, movement transversely to the longitudinal direction can thus be enforced by the cam guided in the guide slots. The cam may, in particular, be configured in the form of a pin which passes through or engages in the guide slots. The guide slots may be of straight-lined and/or curved configuration.

To enable a clip to be received in the clip receptacle, it is advantageous if the tool elements in the clip receiving position assume an open position.

It is also advantageous if the tool elements in the clip spreading position assume an open position. In this way, it is, in particular, possible for free ends of the clamping arms or connecting regions of the clip lying against each other in an applied position to be held at a distance from each other in the clip spreading position.

It may also be advantageous if during transfer from the clip receiving position to the clip spreading position, the tool elements are displaced in the proximal direction relative to the shaft. A spacing between the at least one proximal and the at least one distal clip receiving stop can thus be reduced, in particular, in a simple way during transfer from the clip receiving position to the clip spreading position.

Furthermore, it may be advantageous if the pivot axis about which the tool elements are pivotable relative to the shaft is displaced in the proximal direction during transfer from the clip receiving position to the clip spreading position. In this way, it is possible for the tool elements to execute a superimposed translational-pivotal movement relative to each other and, possibly, relative to the shaft.

To ensure that it is not easy for the clip, in particular, its connecting region, to fall out of the clip receptacle, it is advantageous if the proximal clip receiving stop is configured in the form of a recess into which the connecting region of the clip to be removed is partially insertable. In particular, it is thus possible for movements transversely to a longitudinal direction defined by the spreading device to be prevented in a simple and safe way.

To enable the clip to be received in a simple way, it is advantageous if the recess is open facing in the distal direction. The spreading device with the at least one proximal clip receiving stop can thus be advanced by movement in the distal direction, in particular, towards the connecting region of a simple clip or towards free ends of a double-shank clip.

In accordance with a further preferred embodiment of the invention, it may be provided that the distal clip receiving stop is configured in the form of a clamping jaw recess into which, in particular, a connecting region of the clip to be removed is partially insertable. It is, in particular, thus possible to simply and safely prevent movement of the clip, in particular, of the free ends of its clamping arms or of its connecting regions relative to the spreading device, so that the clip can be held in a defined and safe manner in the clip receptacle. In particular, the clip can thus be held in a defined manner, on the one hand, in the recess and, on the other hand, in the clamping jaw recess or in the clamping jaw recesses.

The clamping jaw recess is preferably open facing in the proximal direction. It can thus face, in particular, in the direction towards the recess which defines the at least one proximal clip receiving stop. It is therefore possible for a clip, without having any undercuts or protruding projections at which it could be alternatively held, to be securely grasped and held, on the one hand, at its connecting region or regions and, on the other hand, in the region of free ends of its clamping arms.

It is advantageous if the spreading device comprises a spreading member facing in the proximal direction, which, in particular, is insertable between two connecting regions of the clamping arms of the clip to be removed. The spreading member can thus face, in particular, in the direction towards the at least one proximal clip receiving stop. In particular, the spreading member may be constructed so as to be movable relative to the at least one proximal clip receiving stop, preferably in the direction towards it, in order to spread the clamping arms of the clip apart as a result of such movement.

A surgical clip can be spread apart particularly easily and safely if the spreading member is wedge-shaped and has a spreading edge facing in the proximal direction. It is thus possible, for example, for the spreading member to be pushed in between two clamping arms lying against each other, starting from their free ends, or between two connecting regions lying against each other, and the free ends or the connecting regions then slide along the wedge-shaped spreading member and can be spread apart.

The spreading device can be constructed in a particularly compact manner if the two tool elements each comprise a spreading member part, and if the spreading member parts form the spreading member. In other words, the spreading member is therefore of two-part construction or of at least two-part construction. In particular, the two spreading member parts may each comprise a distal clip receiving stop or be formed adjacent to such a clip receiving stop.

In order that the spreading device will be of as compact construction as possible in the insertion position, it is advantageous if the spreading member parts in the insertion and/or the clip removal position lie against each other so as to form the spreading member. In particular, it is thus possible to define as small a cross section as possible of the spreading device, so as be able to insert the instrument through a minimally invasive access into a patient's body and withdraw it from the patient's body again.

To improve the tactility of the instrument, it is advantageous if it comprises a first stop device for defining the insertion position. The first stop device may, in particular, be so constructed that a surgeon receives tactile feedback when the instrument assumes the insertion position. He can then ensure, also without visual contact with the spreading device, that, for example, the two tool elements assume a closed position.

In order for the instrument to have a further improved tactility, it is advantageous if it comprises a second stop device for defining the clip removal position. After the clip has been received and spread apart, it is thus possible for a surgeon to transfer the instrument to the clip removal position without having to see the spreading device. Owing to the second stop device, it is, depending on the construction, in particular, also possible to ensure that the instrument cannot be transferred to any other position once it has assumed the clip removal position. In particular, it can thereby be ensured that a clip held in the clip receptacle, which, after having been received and spread apart therein, for example, after removal from the vessel or hollow organ, is closed again, is unable to unintentionally fall out of the clip receptacle.

It is advantageous if the first and/or the second stop device is/are arranged or formed on the actuating device. This has, in particular, the advantage that a very compact construction of the spreading device is possible. In addition, the stop device can be formed on the actuating device, in particular, such that it is not only possible for a surgeon to feel but also to see when the clip removal position is reached. As an alternative, it is, of course, also conceivable to arrange or form the first and/or the second stop device on the shaft or, in particular, also on or in the region of the spreading device.

The first and/or the second stop device is/are preferably configured to delimit a movement of actuating members of the actuating device, which are movable relative to each other. In particular, with an actuating device comprising two or possibly also more actuating members, it is, for example, also possible for the insertion position and/or the clip removal position to be defined by a simple delimitation of the movement of the actuating members relative to each other. The actuating members can be coupled, in particular, to the shaft, on the one hand, and to one or both of the tool elements, on the other hand, so as to also be able to move the tool elements and therefore the clip receiving stops relative to each other as a result of movement of the actuating members relative to each other.

It is advantageous if the actuating members in a farthest possible position from each other define the clip receiving position. It is thus possible for a surgeon to easily transfer the instrument to the clip receiving position by moving the actuating members away from each other.

Furthermore, it may be advantageous if the actuating members in a closest possible position to each other define the clip spreading position. In this way, in particular, the handling of the instrument is improved as a surgeon simply has to move the actuating members towards each other until these cannot be moved any further towards each other. Then he can be sure that the clip is spread apart to the maximum extent and can be easily removed from the vessel or hollow organ.

In accordance with a further preferred embodiment of the invention, it may be provided that the first stop device is arranged or formed such that when transferring from the farthest possible position from each other to the closest possible position to each other, the actuating members assume a defined intermediate position in which the tool elements are closed. It is thus easily possible to design the first stop device such that the instrument assumes the insertion position. In particular, a surgeon is able to tell from the defined intermediate position of the actuating members that the instrument is assuming the insertion position, even if he is not able to see the spreading device directly.

The construction of the instrument is particularly simple if the first stop device comprises an intermediate stop, which is arranged on one of the actuating members and interacts with the other actuating member to define the insertion position. The intermediate stop may, in particular, be arranged stationarily or, alternatively, also movably on the one actuating member. For example, it may be so constructed that it can be moved counter to the action of a restoring member, for example, a compression spring, with a defined restoring force, in particular, in order to transfer the instrument from the insertion position to the clip spreading position. As an alternative, it is also possible for the intermediate stop to be of deformable construction, with a certain force being required to deform it.

It is advantageous for the intermediate stop to be temporarily deactivatable for transfer from the insertion position to the clip spreading position. As explained in the preceding paragraph, the intermediate stop can, for example, be deactivated or disabled in that it can be moved relative to the actuating member on which it is arranged or formed so as to enable movement of the actuating members and therefore also of the instrument from the insertion position to the clip spreading position. In particular, the stop can be formed with a slide surface along which a corresponding projection of the other actuating member can slide and displace the intermediate stop counter to the action of a restoring member. A surgeon is able to feel the effect of the restoring member and so upon increasing a force to move the actuating members, for example, towards each other, he can feel when the instrument assumes the insertion position.

It is advantageous if the intermediate stop comprises an intermediate stop face facing in the distal direction. A defined stop can thus be easily formed. In particular, the intermediate stop face can be formed in the described manner as slide face for moving the intermediate stop when a part of the other actuating member slides along it, for example, in order to release the insertion position.

In accordance with a further preferred embodiment of the invention, it may be advantageous if the second stop device comprises an end stop, which is arranged on one of the actuating members and interacts with the other actuating member to define the clip removal position. In particular, the end stop can be formed in such a way that the instrument can no longer be transferred to the clip spreading or clip receiving position. It can, in particular, thus be ensured that a clip removed from a vessel or hollow organ can be securely held in the clip receptacle when the instrument is pulled out of a patient's body.

It is advantageous for the end stop to be temporarily deactivatable for transfer from the clip removal position to the insertion position. This is of advantage, in particular, when the instrument is configured in the form of a reusable instrument. The instrument blocked permanently, for example, by the second stop device with its end stop can, for example, be configured such that it is only transferable to the insertion position again by corresponding manual intervention. In this way, it can, for example, be ensured that the instrument can only be made ready again for removal of a further clip after safe removal of the clip from the patient's body and removal of the clip from the clip receptacle. For example, temporary deactivation may be brought about by an operator pressing manually against the intermediate stop face, which may be pretensioned in its position by a restoring member.

It is advantageous if the end stop comprises an end stop face facing in the proximal direction. Movement of the actuating members, for example, away from each other or, alternatively, also towards each other can therefore be prevented in a simple and defined way.

The construction of the instrument is particularly simple if the first and second stop devices comprise a projection comprising the intermediate stop face and/or the end stop face. The projection can therefore form, in particular, both the intermediate stop and the end stop, so that only a minimum number of parts is required for forming the instrument.

To prevent a clip removed from a vessel or hollow organ from being able to fall out of the clip receptacle, it is advantageous if the instrument comprises a securing device for securing the instrument in the clip removal position. In particular, the securing device can make it possible to configure the instrument in such a way that it is no longer transferable into any other position once it has reached the clip removal position.

In this way, it is, in particular, possible to prevent a clip received in the clip receptacle from unintentionally falling out of it.

A particularly compact construction of the instrument can be achieved, in particular, by the securing device comprising the second stop device.

The handling of the instrument can be further improved, in particular, by the actuating device and the shaft being rotatable relative to each other about a longitudinal axis of the shaft. This makes it possible for a surgeon to move the shaft and the handle relative to each other in such a way that in a position of the actuating device which is ergonomic for him, he can orientate the spreading device in such a way that a clip can be easily and safely received.

To improve the cleanability, and, in addition, to make the instrument available again more quickly for removal of several clips, it is advantageous if the instrument comprises an instrument handle which is releasably connectable to the shaft and comprises the actuating device. It is, for example, thus possible for the instrument handle and the shaft to be cleaned separately from each other. In addition, the shaft can be optionally released from the instrument handle when a clip has been removed with the instrument. The instrument handle can then be connected to a further shaft, which is already ready again to receive a clip, while the shaft with which a clip has just been removed can be made ready to receive a further clip, in particular, by removing the clip from the clip receptacle.

A surgical instrument generally designated by reference numeral 10 for removing a surgical clip 12 applied to a hollow organ is diagrammatically represented in FIG. 1. In particular, the clip 12 can be configured in the form of a double-shank clip shown in FIG. 2, which comprises four clamping arms 14, lying one against the other in pairs, which have four free ends 16 connected in pairs and four ends 20 also connected to one another in pairs, each defining a connecting region 18. The instrument 10 has a proximal end 22 and a distal end 24.

The instrument 10 comprises an instrument handle 26 which is releasably connectable to an elongate tubular shaft 28. The instrument handle 26 and the shaft 28 are rotatable relative to each other about a longitudinal axis 30 defined by the shaft 28. A connection between instrument handle 26 and shaft 28 is established by a coupling part 32 held so as to be movable on the instrument handle 26.

The instrument handle 26 comprises an actuating device 34 having a first actuating member 36 in the form of an arm fixedly connected to an instrument handle base body 38 and projecting substantially transversely to the longitudinal axis 30, and a second, arm-shaped actuating member 42 pivotable on the instrument handle base body 38 about a pivot axis 40 extending perpendicularly to the longitudinal axis 30, which is mounted so as to project somewhat further in the proximal direction. Free ends of the first and second actuating members 36, 42 are configured in the form of finger rings 44 and 46, respectively.

The actuating device 34 serves to transmit an actuating force via a force-transmitting member 48, which is movably coupled to the second actuating member 42 and is in the form of a push-and-pull rod mounted so as to be displaceable and rotatable in the shaft 28, onto two tool elements 50 of a spreading device 52 for grasping and spreading apart an applied clip 12 from an applied position to a released position, which are movably mounted at the distal end of the shaft and are of identical construction, but are arranged so as to be turned relative to each other through 180° about the longitudinal axis 30. A distal end of the force-transmitting member 48 is configured in the form of a bearing jaw 54 having a transverse bore in which is held a bearing pin 58, which is inserted coaxially with a pivot axis 56 extending perpendicularly to the longitudinal axis 30.

The bearing jaw 54, facing in the distal direction, projects beyond a bottom 60 of a substantially U-shaped tool element receptacle 62, which is constructed mirror-symmetrically in relation to a mirror plane containing the longitudinal axis 30 and comprises two opposed side legs 64 which have inside walls 66 parallel to each other. Formed in each of the end faces 68, facing in the distal direction, of the legs 64 is a transverse groove 70 in which a substantially cuboidal proximal clip receiving stop 72 is inserted, which has a recess 74 facing in the distal direction. Somewhat proximally of the transverse groove 70, a round rod-shaped cam 76 is inserted in transverse bores of the legs 64.

Starting from their proximal end 78, the tool elements 50 have a substantially semicircular recess 80, facing in the proximal direction and in the direction towards the longitudinal axis 30, which is additionally provided with a transverse bore 82. The two tool elements further comprise, somewhat distally of the center, through-openings 84 curved in substantially semicircular configuration and extending transversely to the longitudinal axis 30, which form guide slots 86 of a connecting link guide 89 in the form of a slot-cam-guide, generally designated by reference numeral 88. The two tool elements 50 lie with inside surfaces 90 one against the other and with outside surfaces 92, extending parallel to these inside surfaces 90, against the inside walls 66 of the legs 64. The bearing pin 58 projecting on both sides beyond the bearing jaw 54 engages the transverse bores 82 and thus movably couples the tool elements 50 to the force-transmitting member 48. The cam 76 is guided in the guide slots 86, so that movement of the force-transmitting member 48 in the proximal or distal direction results in a forced pivotal movement of the tool elements 50 about the common pivot axis 56. As a result of movement of the force-transmitting member 48 in the proximal direction, the pivot axis 56 is, in turn, also moved in the proximal direction. Movement of the force-transmitting member 48 in the distal direction automatically causes the bearing pin 58 and therefore also the pivot axis 56 to be moved in the distal direction.

Distal end sections 94 of the tool elements 50 define, in a closed position in which contact surfaces 96 facing each other lie one against the other, a spreading member 100 having a spreading edge 98 facing in the proximal direction. The spreading member 100 is formed in two parts, namely by two spreading member parts 102, each formed on one of the two tool elements 50. In particular, the spreading member parts 102 are delimited at the sides by the contact surfaces 96. Starting from the spreading edge 98, each tool element 50 defines a clamping jaw recess 104 facing in the proximal direction. The clamping jaw recesses 104 define center planes 106 which open away from each other in the distal direction. Somewhat proximally of the spreading edge 98, the tool elements 50 have side faces 108 facing each other, but spaced from each other, which each have on one side an edge 110 extending parallel to the longitudinal axis 30. A height of the edge 110 corresponds approximately to half the distance between the side faces 108 when the contact surfaces 96 lie one against the other. A clip receptacle 112 of the spreading device 52 is defined by the side faces 108 and the recess 74 and the clamping jaw recess 104. The edges 110 close the clip receptacle 112 at the sides at least partially.

Arranged proximally of the legs 64 and coaxially with the longitudinal axis 30 is a guide sleeve 114, which projects in the proximal direction and has a longitudinal bore through which the force-transmitting member 48 extends. The guide sleeve 114 is adjoined proximally by a coupling section 116 with which the spreading device 52 is optionally releasably connectable to the shaft 28.

Figure 2:
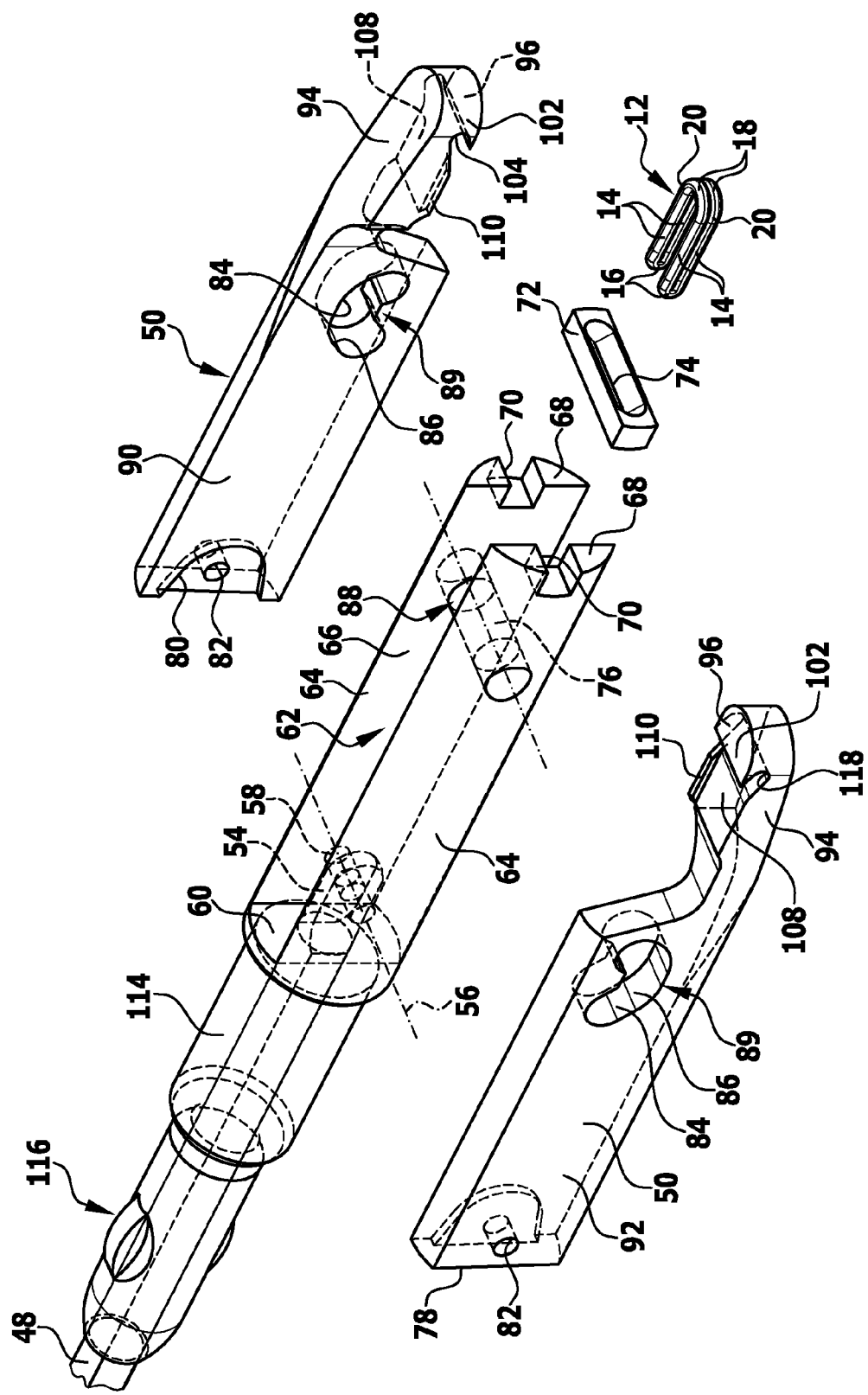
FIG. 2 shows an exploded representation of a spreading device of the instrument from FIG. 1.
Figure 3:
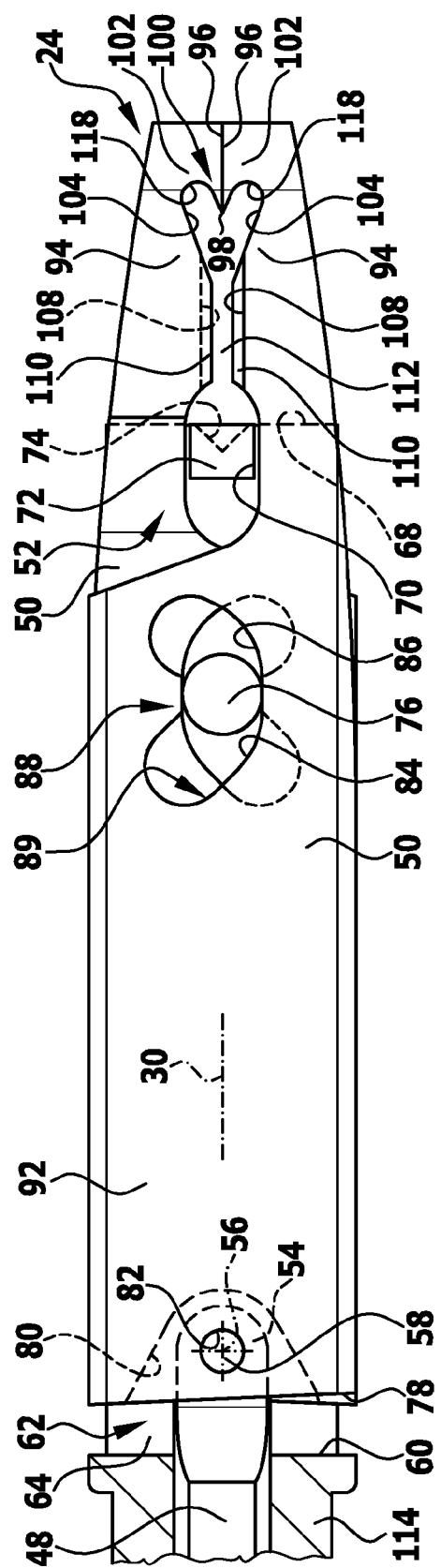
FIG. 3 shows a partly cut-away longitudinal sectional view of the spreading device in the insertion position.
Figure 4:
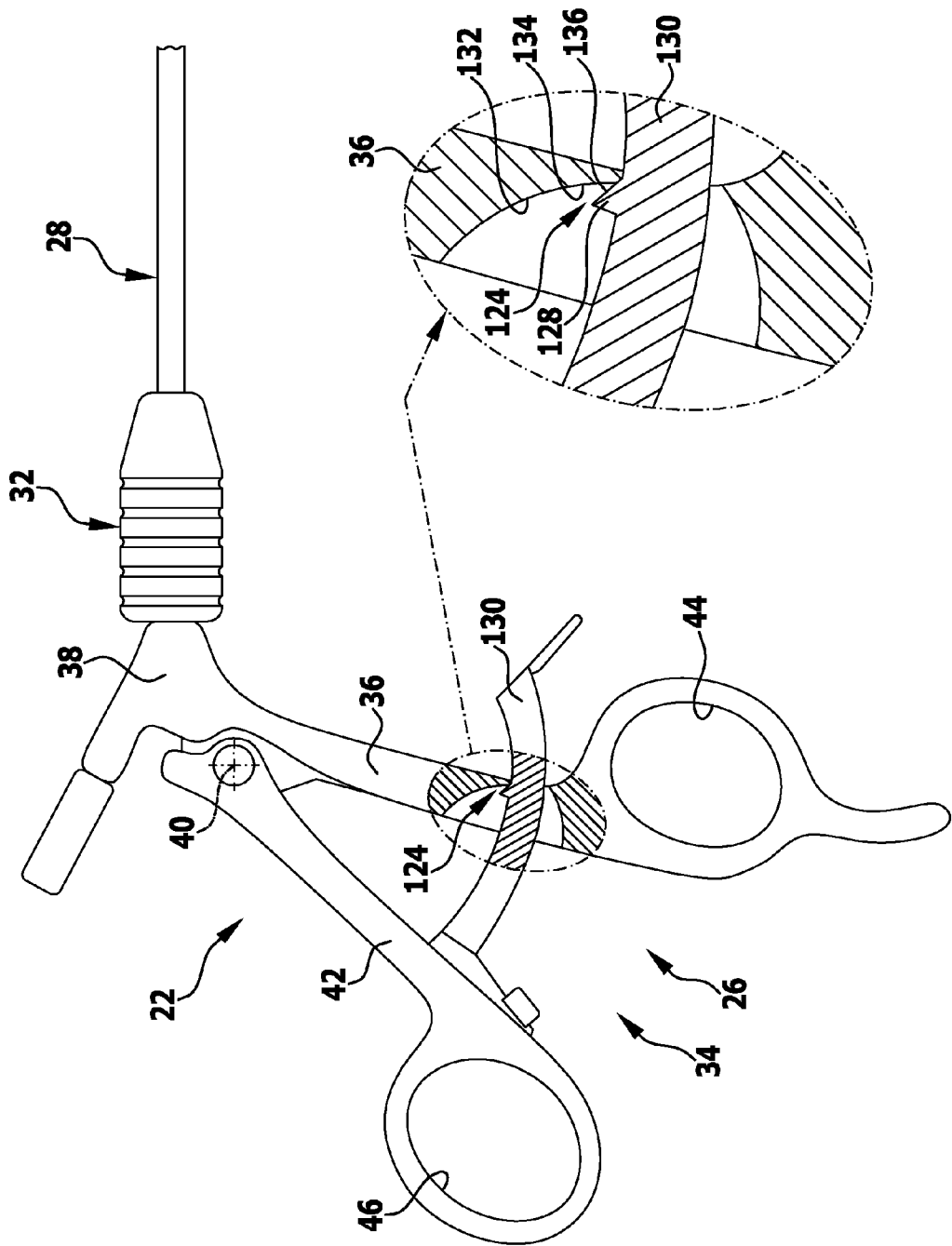
FIG. 4 shows a partly cut-away longitudinal sectional view of the instrument handle in the insertion position.

The clip 12, as shown, for example, in FIG. 2, is in the form of a double-shank clip, where the free ends 16 of the clamping arms 14 are connected to free ends 16 of two further clamping arms 14 whose opposite free ends are, in turn, connected to each other by a connecting region 18. In a plan view, the clip 12 is of substantially U-shaped configuration, with the clamping arms 14, which are connected to each other by the connecting region 18, extending parallel to each other and being spaced from each other. The clamping arms 14, connected to each other by their free ends 16, lie, in an applied position of the clip 12, with surface-to-surface contact one against the other, as do the connecting regions 18. The clip 12 is made of a self-contained material which is formed essentially in the shape of wire. In a plan view, the clip 12 is open in the direction towards the free ends 16. In a side view, the clip 12 is open facing in the direction towards the connecting regions 18, and, as mentioned above, in the side view the clamping arms 14 connected by the free ends 16 lie with surface-to-surface contact against each other.

The clip receptacle 12 is configured such that the free ends 16 can engage the recess 74, and the connecting regions 18 can each engage one of the distal clip receiving stops 118 defined by the clamping jaw recess 104. The proximal and distal clip receiving stops 72 and 118 delimit the clip receptacle 112 proximally and distally, respectively. The proximal and distal clip receiving stops 72, 118 define between them a spacing 120. The two distal clip receiving stops 118 define between them a transverse spacing 122.

The instrument 10 further comprises a first stop device, generally designated by reference numeral 124, and a second stop device, generally designated by reference numeral 126. Both stop devices 124 and 126 are arranged or formed on the actuating device 34. They serve to delimit movement of the actuating members 36 and 42 relative to each other.

The first stop device 124 comprises an intermediate stop 128 which is arranged on a lever arm 130, curved concavely in relation to the pivot axis 40, so as to project in the direction towards the pivot axis 40. The lever arm 130 is arranged so as to project from the second actuating member 42 in the direction towards the first actuating member 36 and passes through a through-opening 132 formed in the actuating member 36. The intermediate stop 128 therefore interacts with the first actuating member 36, namely with a side face 134 of the actuating member 36, which faces in the proximal direction and extends as far as the through-opening 132. The intermediate stop 128 comprises an intermediate stop face 136 facing substantially in the distal direction, which is inclined somewhat in the direction towards the longitudinal axis 30. It forms a slide surface for the side face 134. Preferably, the intermediate stop 128 is displaceable, in a manner not shown, counter to the action of a restoring member, for example, a helical spring, in the direction towards the lever arm 30 and into it when the side face 134 slides along the intermediate stop face 136. The intermediate stop 128 thus defines a pressure point which can be felt by an operator.

The second stop device 126 comprises an end stop 138 which is defined by a projection 140 which also forms the intermediate stop 128. The end stop 138 comprises an end stop face 142 facing in the proximal direction, which is formed so as to project substantially perpendicularly from the lever arm 130. It interacts with a side face 144, facing in the distal direction, of the first actuating member 36.

The end stop 138 is temporarily deactivatable. To this end, it must be moved manually in the direction towards the lever arm 130 and into it, for example, counter to the action of the described restoring member. Temporary deactivation of the intermediate stop 128 occurs automatically on moving the second actuating member 42 in the direction towards the first actuating member 36 when the side face 134 slides along the intermediate stop face 136 and moves the intermediate stop 128 counter to the action of the restoring member in the direction towards the lever arm 130.

Owing to the special configuration of the second stop device 126, it also comprises a securing device 146, which prevents the second actuating member 42 from being able to be moved further in the direction towards the first actuating member 36 when the side face 144 strikes the end stop face 142.

The way in which the instrument operates will be explained in greater detail below, in particular, in conjunction with FIGS. 3 to 10.

To remove a clip 12 applied to a vessel or hollow organ, the instrument 10 must first be inserted with its spreading device 52, for example, through a minimally invasive access into a patient's body and advanced towards the clip 12 to be removed. For this purpose, the instrument 10 is transferred to the insertion position shown diagrammatically in FIGS. 3 and 4. To do so, starting from a position of the tool elements 50, as shown in FIG. 5, in which they are open to the maximum extent, the second actuating member 42 is moved in the direction towards the first actuating member 36 until the side face 134 strikes the intermediate stop face 136. A surgeon can feel this as the pressure point described above. In this insertion position, the contact surfaces 96 lie with surface-to-surface contact against each other. The cam 76 assumes an intermediate position in the two guide slots 86, as shown diagrammatically in FIG. 3.

The spreading device 52 is transferable from the insertion position in which the clip receptacle 112 defines a minimal cross-sectional area to the clip receiving position, shown diagrammatically in FIGS. 5 and 6, in which the clip receptacle 112 is open to receive the clip 12 to be removed. To this end, the second actuating member 42 is pivoted away from the first actuating member 36. In the clip receiving position, the actuating members 36 and 42 are spaced as far as possible from each other. With the proximal clip receiving stop 72, the spreading device 52 is then advanced towards the clip 12 such that the free ends 16, as diagrammatically clearly recognizable in the exploded representation in FIG. 2, can engage the recess 74.

Figure 7:
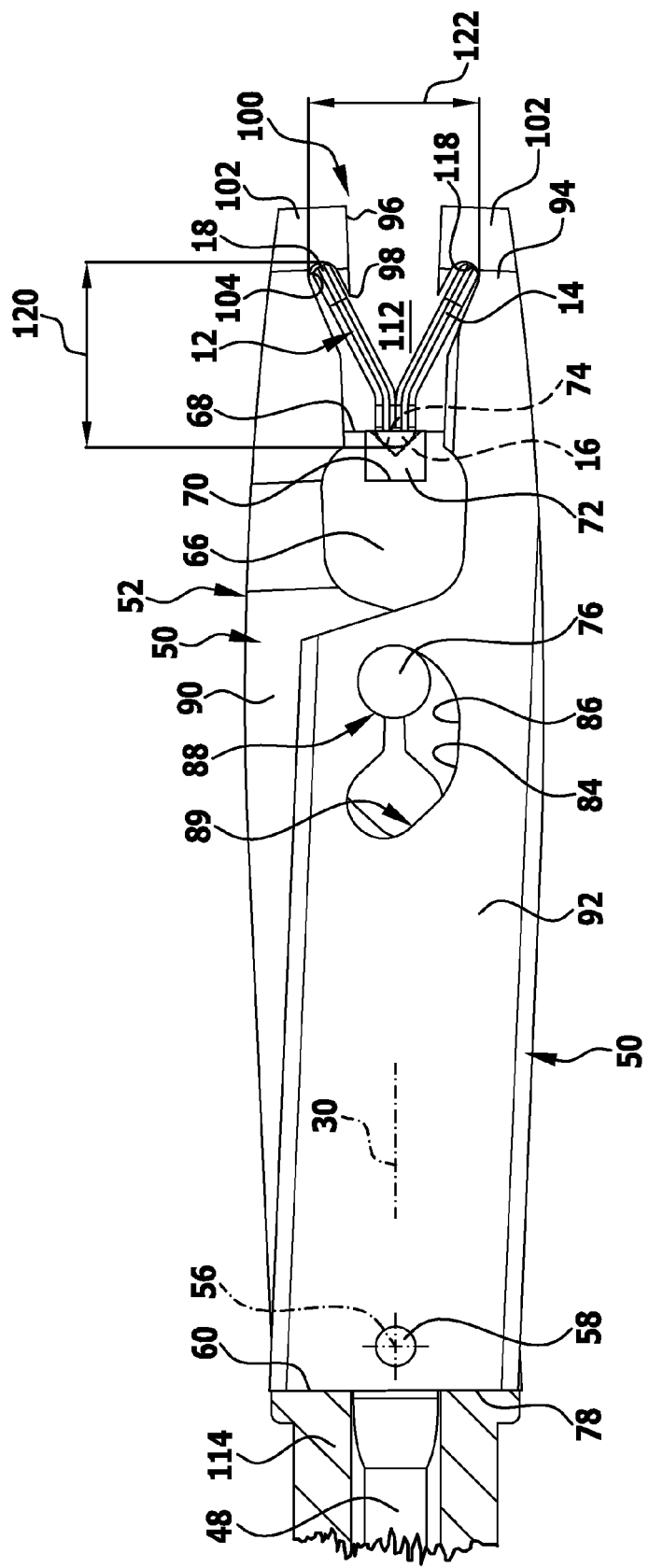
FIG. 7 shows a view of the spreading device in analogy with FIG. 3 in the clip spreading position.
Figure 8:
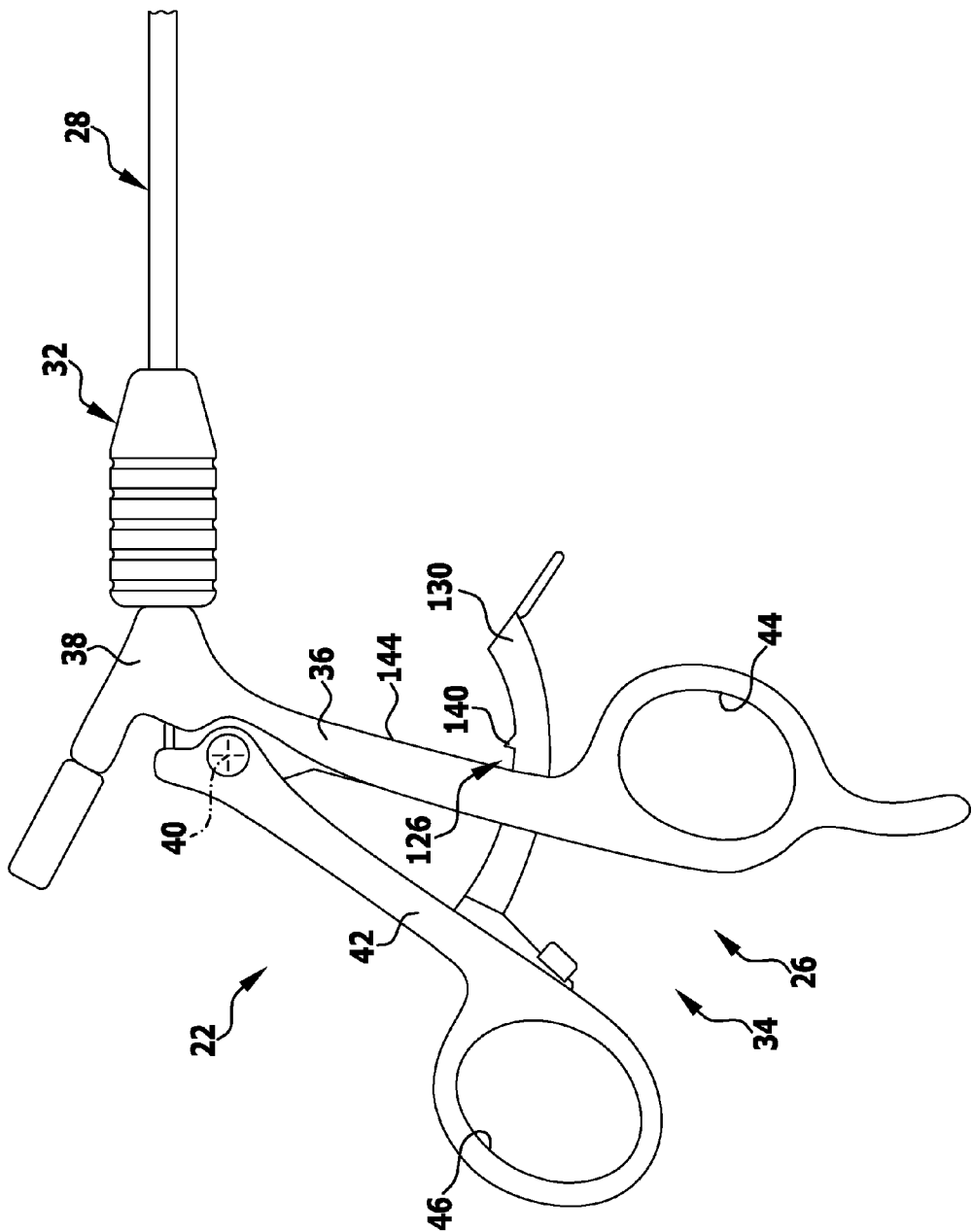
FIG. 8 shows a view of the instrument handle in analogy with FIG. 4 in the clip spreading position.

In the next step, the instrument 10 is transferred from the clip receiving position to the clip spreading position, which is shown diagrammatically in FIGS. 7 and 8. To this end, after advancing the free ends 16 towards the recess 74, the second actuating member 42 is moved in the direction towards the first actuating member 36, namely beyond the described pressure point defined by the first stop device 124 to a position of the actuating members 36 and 42 in which they are as close as possible. As a result of the movement of the actuating members 36 and 42 towards each other, the force-transmitting member 48 is also moved in the proximal direction, and the cam 76 travels from a proximal end position in the guide slots 86 to a distal end position, as shown diagrammatically in FIG. 7.

In the clip spreading position, the tool elements 50 are spread not quite as far apart as in the clip receiving position. During transfer from the clip receiving position to the clip spreading position, the spreading device 52 passes through the insertion position. During transfer from the clip receiving position to the clip spreading position, the distal clip receiving stops 118 move in the direction towards the proximal clip receiving stop 72 so that the spacing 120 becomes increasingly smaller. The connecting regions 18, which each engage a clamping jaw recess 104, are thereby forced to move away from each other as the transverse spacing 122 becomes successively larger when proceeding from the insertion position to the clip spreading position. The spreading-apart is facilitated, in particular, by the spreading member 100, which engages between the connecting regions 18 and guides these into the clamping jaw recesses 104.

The clip 12 held spread apart in the clip receptacle 112, as shown in FIG. 7, can now be removed from the vessel or hollow organ without damaging it.

Figure 9:
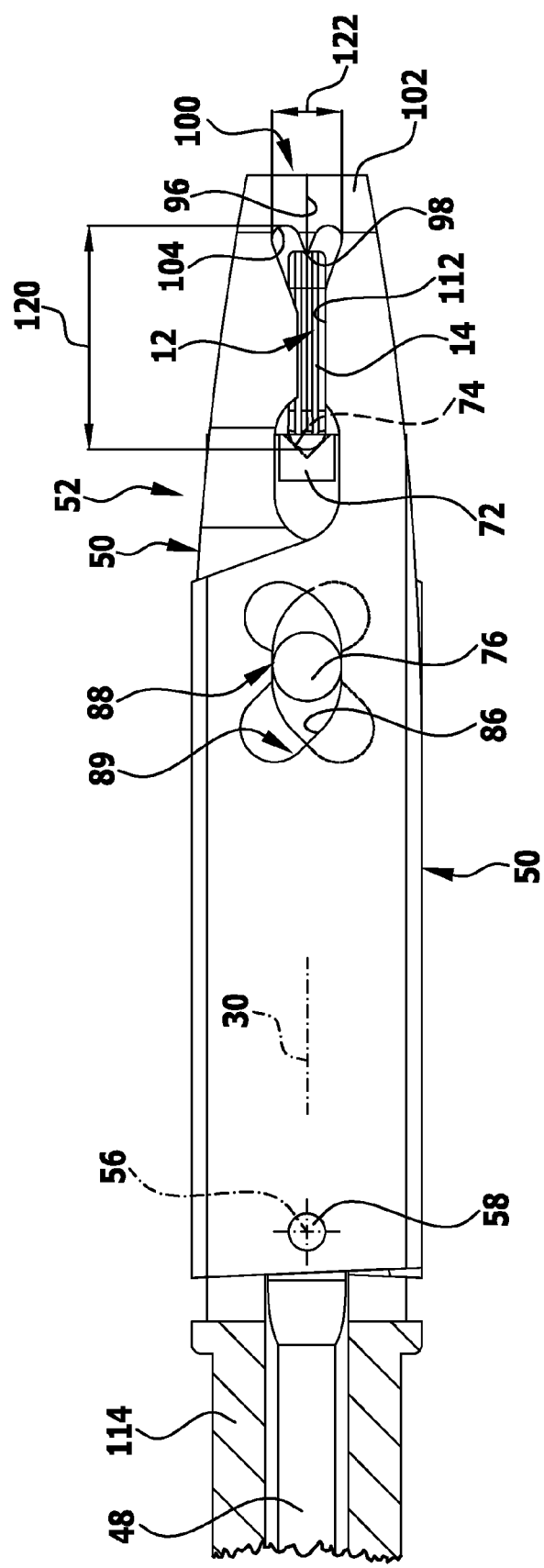
FIG. 9 shows a view of the spreading device in analogy with FIG. 3 in the clip removal position.
Figure 10:
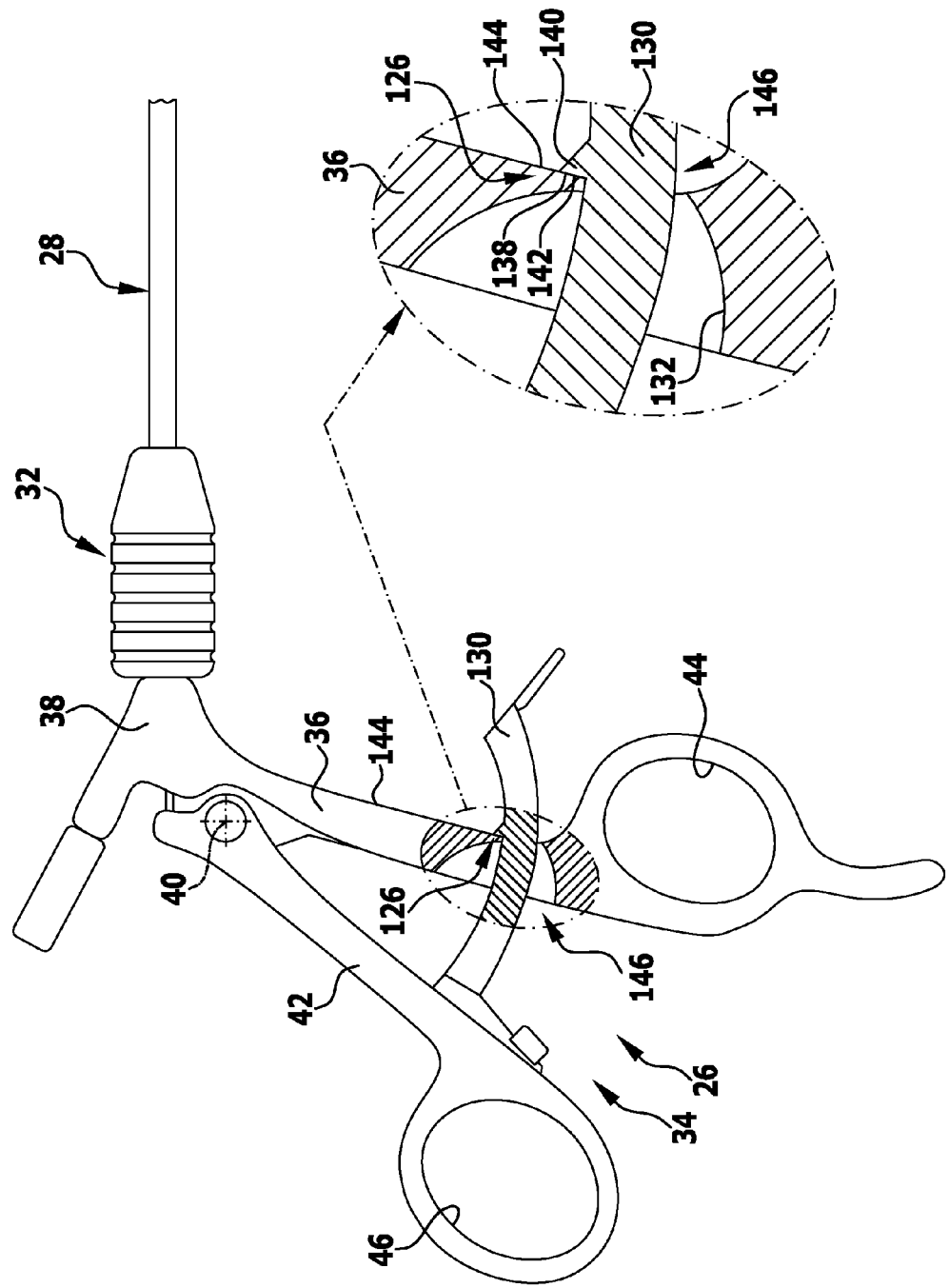
FIG. 10 shows a view of the instrument handle in analogy with FIG. 4 in the clip removal position.

Since it may not be possible for the spread-apart tool elements 50 to be removed through an access of small cross section, in particular, in the case of minimally invasive use of the instrument 10, the instrument 10 can be transferred to the clip removal position shown in FIGS. 9 and 10. To do so, starting from the clip spreading position, the second actuating member 42 is pivoted away from the first actuating member 36 again, namely until the side face 144 strikes the end stop face 142. The cam 76 then again assumes an intermediate position in the guide slots 86, and the contact surfaces 96 lie with surface-to-surface contact against each other. During transfer to the clip removal position, the clip 12 is closed again, i.e., its clamping arms lie against each other in pairs again. The clip receptacle 112 is closed at the proximal side and the distal side by the proximal and distal clip receiving stops 72 and 118, respectively. Owing to the edges 110, it is not possible for the clip 12 to get out of the clip receptacle 112 at the sides, so that the clip 12 can be extracted from the patient's body without being able to fall out of the clip receptacle 112.

To prepare the instrument 10 for removal of a further clip 12, the second stop device 126 must be temporarily deactivated, namely by temporarily disabling the end stop 138, so that the actuating members 36 and 42 can be moved again into their position in which they are spread apart or spaced as far as possible from each other, as represented diagrammatically in FIG. 6. The clip receptacle 112 then opens due to pivoting of the tool elements 50 away from each other, so that the clip 12 removed from the patient's body can be taken out of the clip receptacle 112.

Figure 11:
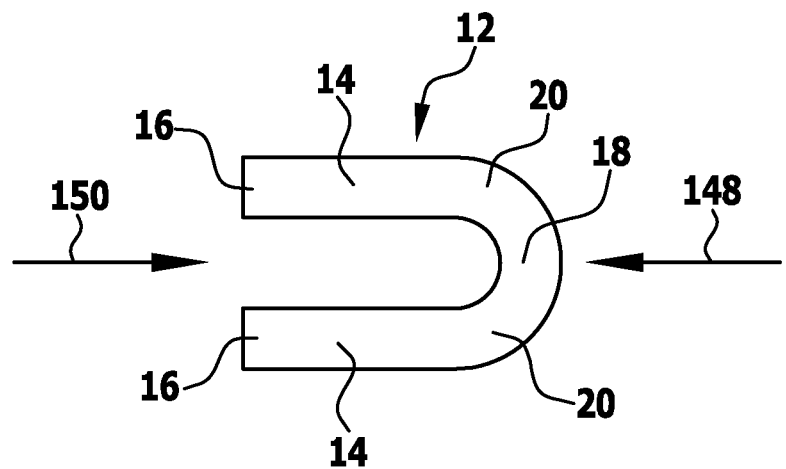
FIG. 11 shows a diagrammatic representation of the procedure when removing a surgical clip.
Figure 12:
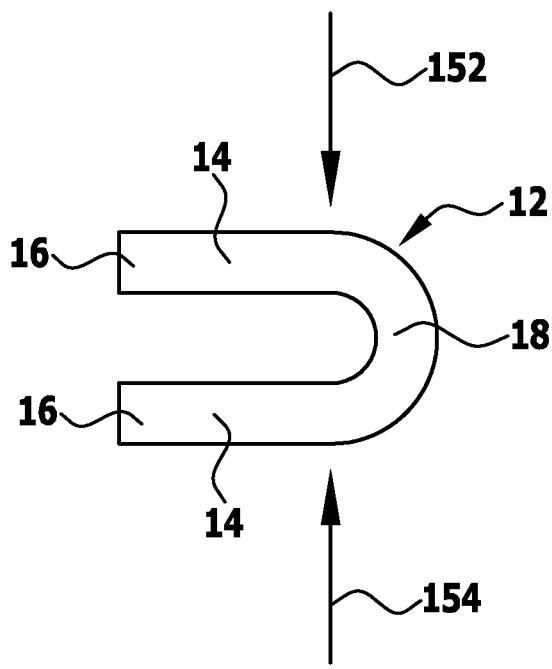
FIG. 12 shows a diagrammatic representation of an alternative variant for removal of a clip.

The interaction of the spreading device 52 with the applied clip 12 which is to be removed is represented diagrammatically in FIG. 11. The clip 12 shown in a plan view in FIG. 12 can be spread apart in the described manner by moving the proximal clip receiving stop 72 in the direction of arrow 150, i.e., in the distal direction, and by moving the distal clip receiving stops 118 in the direction of arrow 148, i.e., in the proximal direction.

Alternatively, it is, however, also conceivable to configure the spreading device 52 in such a way that the clip 12 is not held between its free ends 16 and the connecting regions 18 in the clip receptacle 112, but between the two opposite clamping arms 14 lying in pairs against each other. This is represented diagrammatically in FIG. 12, in which the clip 12 is also shown in a plan view. A spreading-apart can be brought about, in particular, by introducing in the direction of arrows 152 and 154 towards each other two spreading members which face each other and are similar in construction to the spreading members 100 and which directly engage between the clamping arms 14 lying against each other and spread these apart.

Figure 13:
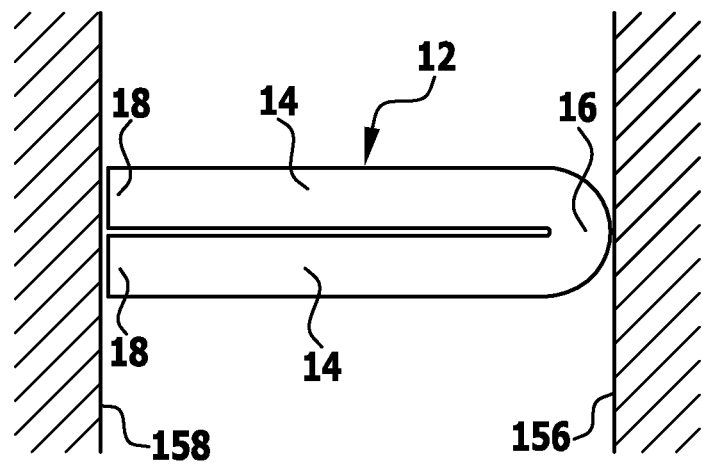
FIG. 13 shows a diagrammatic representation of a closed clip prior to removal by squeezing it open.
Figure 14:
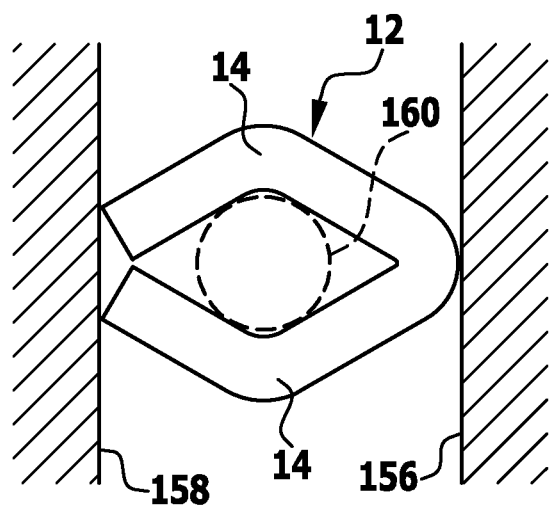
FIG. 14 shows a diagrammatic representation of the clip squeezed open.

An alternative, manual procedure for releasing the clip 12 from a vessel or hollow organ is represented diagrammatically in FIGS. 13 and 14. The clip 12 is advanced with its free ends 16 towards a clamping jaw 156 and with the connecting regions 18 towards a clamping jaw 158. The clamping jaws 156 and 158 having clamping jaw surfaces extending parallel to each other are moved towards each other and the clip 12 is thus forcibly squeezed open, namely by deformation of the clamping arms 14, so that these are partially moved apart and thereby release a hollow organ or vessel 160 originally clamped between them.

The instrument 10 can be easily cleaned, namely by the instrument handle 26 being separated from the shaft 28. Optionally, the shaft 28 can also be released from the spreading device 52.

Furthermore, it is conceivable to transfer the clip 12, after removal from a vessel, not outside the patient's body, but inside it to another suitable instrument, when the clip 12 is removed from the surgical site. With the other instrument, the clip 12 can then be removed in the clip receiving position from the clip receptacle 112.

The invention claimed is:

1. Surgical instrument for removing a surgical clip applied to a hollow organ, said clip comprising two clamping arms having two free ends and two ends connected to each other and defining a connecting region, and said surgical instrument comprising:
   a proximal and a distal end,
   a spreading device for grasping and spreading apart an applied clip from an applied position to a released position arranged at the distal end,
   the spreading device comprising a clip receptacle and at least one proximal clip receiving stop and at least one distal clip receiving stop which respectively delimit the clip receptacle at a proximal side and at a distal side,
   wherein:
   the spreading device is transferable from an insertion position in which the spreading device defines a minimal cross-sectional area to a clip receiving position in which the clip receptacle is open to receive the clip to be removed, and
   a spacing in a longitudinal direction between the at least one proximal clip receiving stop and the at least one distal clip receiving stop decreases during transfer of the spreading device from the clip receiving position to a clip spreading position.

2. Surgical instrument in accordance with claim 1, wherein in the clip spreading position the clip to be removed is held spread apart in the clip receptacle.

3. Surgical instrument in accordance with claim 1, wherein the spreading device is transferable from the clip spreading position in which the clip to be removed is held spread apart in the clip receptacle to a clip removal position in which the clip to be removed is held closed in the clip receptacle.

4. Surgical instrument in accordance with claim 3, further comprising a second stop device for defining the clip removal position.

5. Surgical instrument in accordance with claim 3, further comprising a securing device for securing the instrument in the clip removal position.

6. Surgical instrument in accordance with claim 1, wherein the at least one distal clip receiving stop comprises two distal clip receiving stops.

7. Surgical instrument in accordance with claim 6, wherein a transverse spacing between the two distal clip receiving stops increases transversely to the longitudinal direction during transfer from the clip receiving position to the clip spreading position.

8. Surgical instrument in accordance with claim 1, wherein:
   the spreading device comprises two tool elements movable relative to each other, and
   the at least one distal clip receiving stop is arranged or formed on the two tool elements.

9. Surgical instrument in accordance with claim 8, further comprising a shaft with the spreading device arranged at a distal end of the shaft,
   wherein the two tool elements are mounted so as to be at least one of displaceable and pivotable relative to the shaft.

10. Surgical instrument in accordance with claim 9, wherein the tool elements are displaced in a proximal direction relative to the shaft during transfer from the clip receiving position to the clip spreading position.

11. Surgical instrument in accordance with claim 9, wherein a pivot axis about which the tool elements are pivotable relative to the shaft is displaced in a proximal direction during transfer from the clip receiving position to the clip spreading position.

12. Surgical instrument in accordance with claim 8, wherein:
   the two tool elements are movably coupled to a force-transmitting member for moving the tool elements relative to each other as a result of movement of the force-transmitting member, and the force-transmitting member is mounted so as to be movable in or on the shaft.

13. Surgical instrument in accordance with claim 8, wherein the tool elements in the clip spreading position assume an open position.

14. Surgical instrument in accordance with claim 1, wherein the at least one proximal clip receiving stop is configured in the form of a recess into which the free ends of the clip to be removed are partially insertable.

15. Surgical instrument in accordance with claim 1, wherein the at least one distal clip receiving stop is configured in the form of a clamping jaw recess into which the connecting region of the clip to be removed is partially insertable.

16. Surgical instrument in accordance with claim 1, wherein the spreading device comprises a spreading member facing in a proximal direction, which is insertable between two connecting regions of the clamping arms of the clip to be removed.

17. Surgical instrument in accordance with claim 1, further comprising a first stop device for defining the insertion position.

18. Surgical instrument in accordance with claim 17, wherein at least one of the first stop device and a second stop device is arranged or formed on an actuating device of the surgical instrument.

19. Surgical instrument in accordance with claim 17, wherein at least one of the first and the second stop devices is configured to delimit a movement of actuating members of the actuating device, which are movable relative to each other.

20. Surgical instrument in accordance with claim 19, wherein:
the spreading device comprises two tool elements movable relative to each other, and
the first stop device is arranged or formed such that when transferring the stop devices from the farthest possible position from each other to the closest possible position to each other, the actuating members assume a defined intermediate position in which the tool elements are closed.

21. Surgical instrument in accordance with claim 19, wherein the first stop device comprises an intermediate stop, which is arranged on one of the actuating members and interacts with the other actuating member to define the insertion position.

22. Surgical instrument in accordance with claim 21, wherein the intermediate stop comprises an intermediate stop face facing in a distal direction.

\* \* \* \* \*